US00PP08701P

United States Patent [19]

Thome

[11] Patent Number: Plant 8,701

[45] Date of Patent: Apr. 26, 1994

[54] APPLE TREE TF812

[75] Inventor: Harold Thome, Comstock Park, Mich.

[73] Assignee: Inter-Plant Patent Marketing, Inc., Niagara-On-The-Lake, Canada

[21] Appl. No.: 777,780

[22] Filed: Oct. 11, 1991

[51] Int. Cl.[5] ..... A01H 5/00

[52] U.S. Cl. ..... Plt./34.1

[58] Field of Search ..... Plt. 34.1

[56] References Cited

U.S. PATENT DOCUMENTS

Plt. 851 1/1934 Uecker ..... Plt./34.1
Plt. 2650 7/1966 Snyder ..... Plt./34.1
Plt. 2934 10/1969 Robison, et al ..... Plt./34.1
Plt. 5086 8/1983 Carnefix ..... Plt./34.1
Plt. 5838 12/1986 Akins ..... Plt./34.1
Plt. 6406 11/1988 Higgins ..... Plt./34.1

*Primary Examiner*—James R. Feyrer
*Attorney, Agent, or Firm*—Dykema Gossett

[57] ABSTRACT

A new and distinct variety of apple tree originated as a whole-tree mutation of "NuRed Jonathan." The fruit of the new variety is of a more strikingly intense red coloration, fruit is of a larger size, and that fruit has a higher sugar content sooner than the parent variety, allowing for advantageous earlier harvest of the fruit.

5 Drawing Sheets

FIELD OF THE INVENTION

The present invention relates generally to apple trees and, more specifically, to a whole-tree mutation of an apple variety marketed as "NuRed Jonathan".

BACKGROUND OF THE INVENTION

A popular type of apple tree, the Snyder cultivar of U.S. Plant Pat. No. 2,650, the disclosure of which is incorporated herein by reference and which is sold under the name "Nured Jonathan" had been grown in an orchard of Thome Farms at 2137 Seven Mile Road, in the City of Comstock Park, State of Michigan. In the fall of 1986, at that location, a whole tree mutation of the aforementioned Snyder cultivar (hereinafter, "parent variety") was discovered which has been named TF812. This new variety has a number of unique and desirable characteristics which distinguish it from the parent variety as well as from the Higred cultivar (U.S. Plant Pat. No. 6,406), and the Super Jon cultivar (U.S. Plant Pat. No. 5,086).

STATEMENT OF ASEXUAL PROPAGATION

The new cultivator, TF812, has been asexually propagated at 2137 Seven Mile Road, in the City of Comstock Park, State of Michigan by grafting and has been observed to remain true to the description set forth herein.

SUMMARY OF THE INVENTION

The new apple cultivar of the present invention, known as TF812, was found in a solid row of apple trees sold as "NuRed Jonathan," (hereinafter "parent variety") and is a whole-tree mutation thereof. It differs from the parent in that TF812 develops a markedly increased red fruit color at maturity in comparison with the parent variety.

DETAILED BOTANICAL DESCRIPTION

Figure 1:
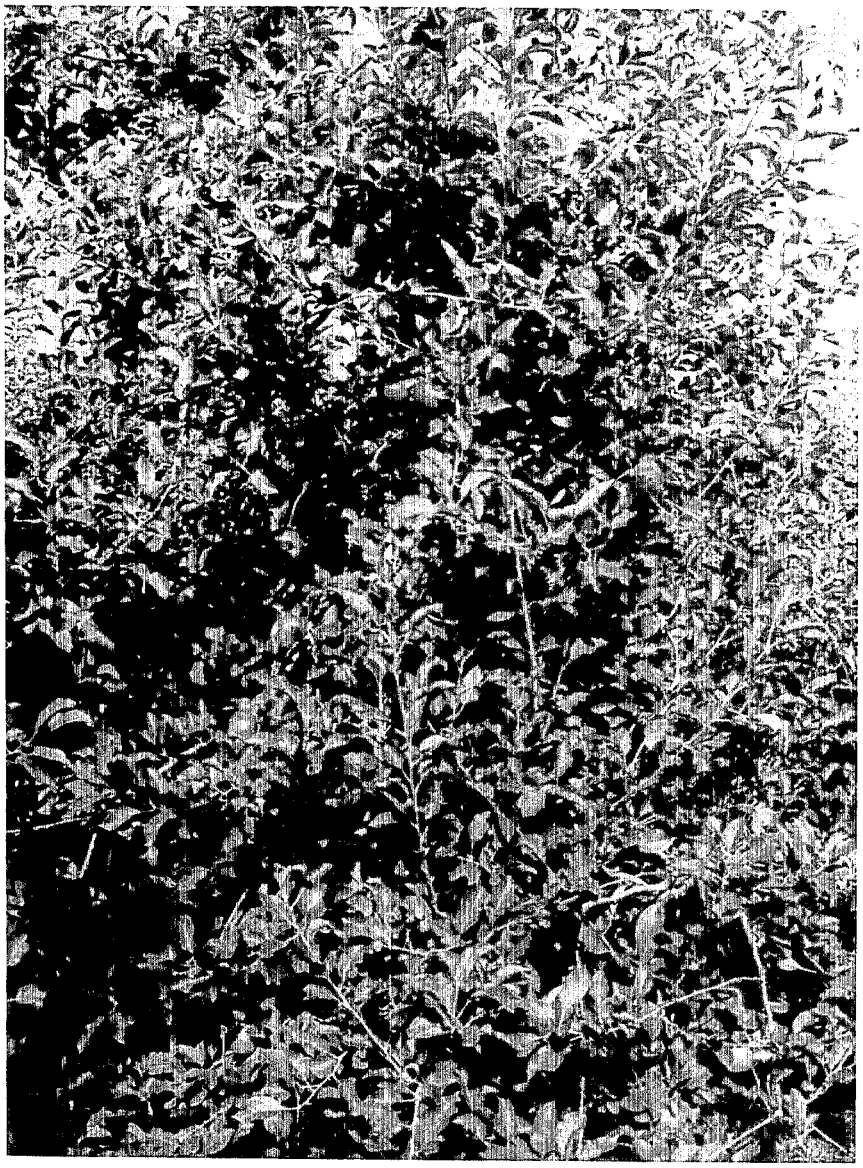
FIG. 1 depicts a whole tree view of TF812.
Figure 2:
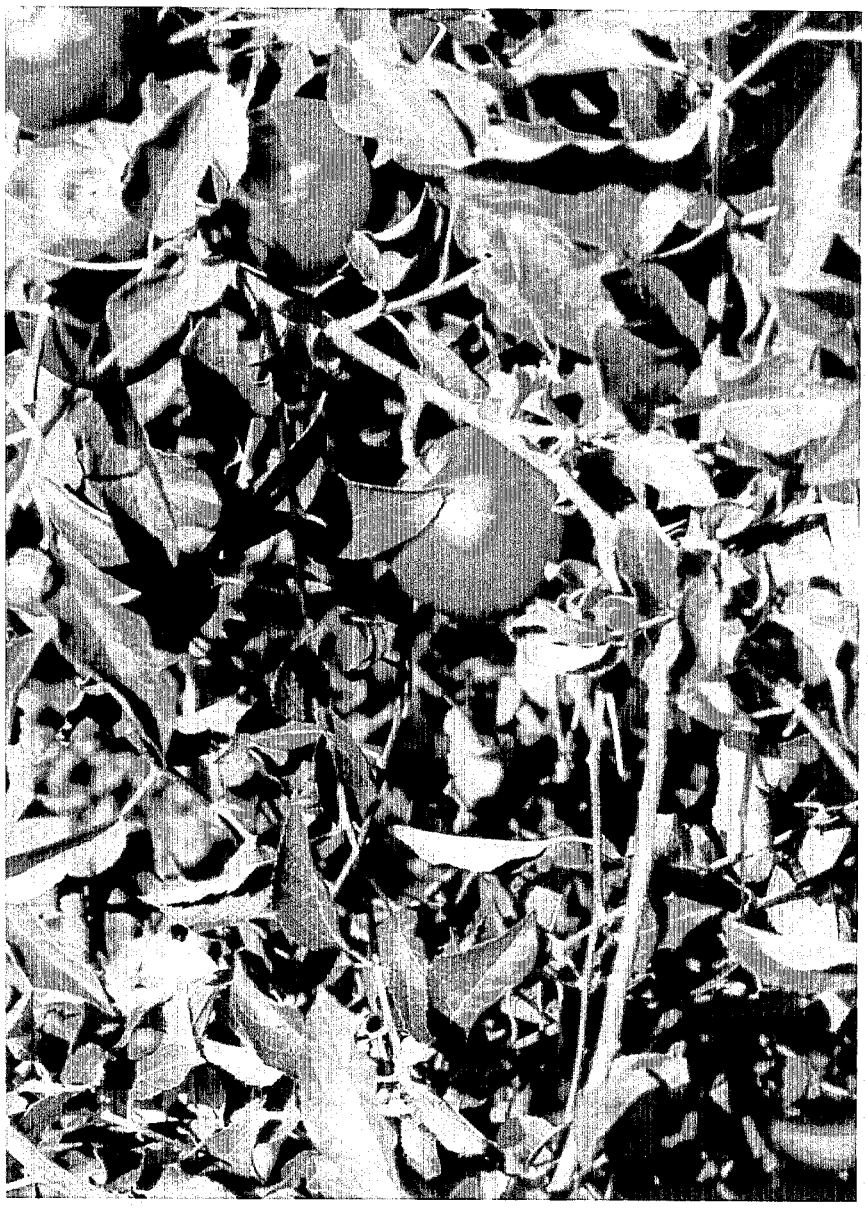
FIG. 2 depicts a branch of TF812 which illustrates the fruit and leaves of TF812.
Figure 3:
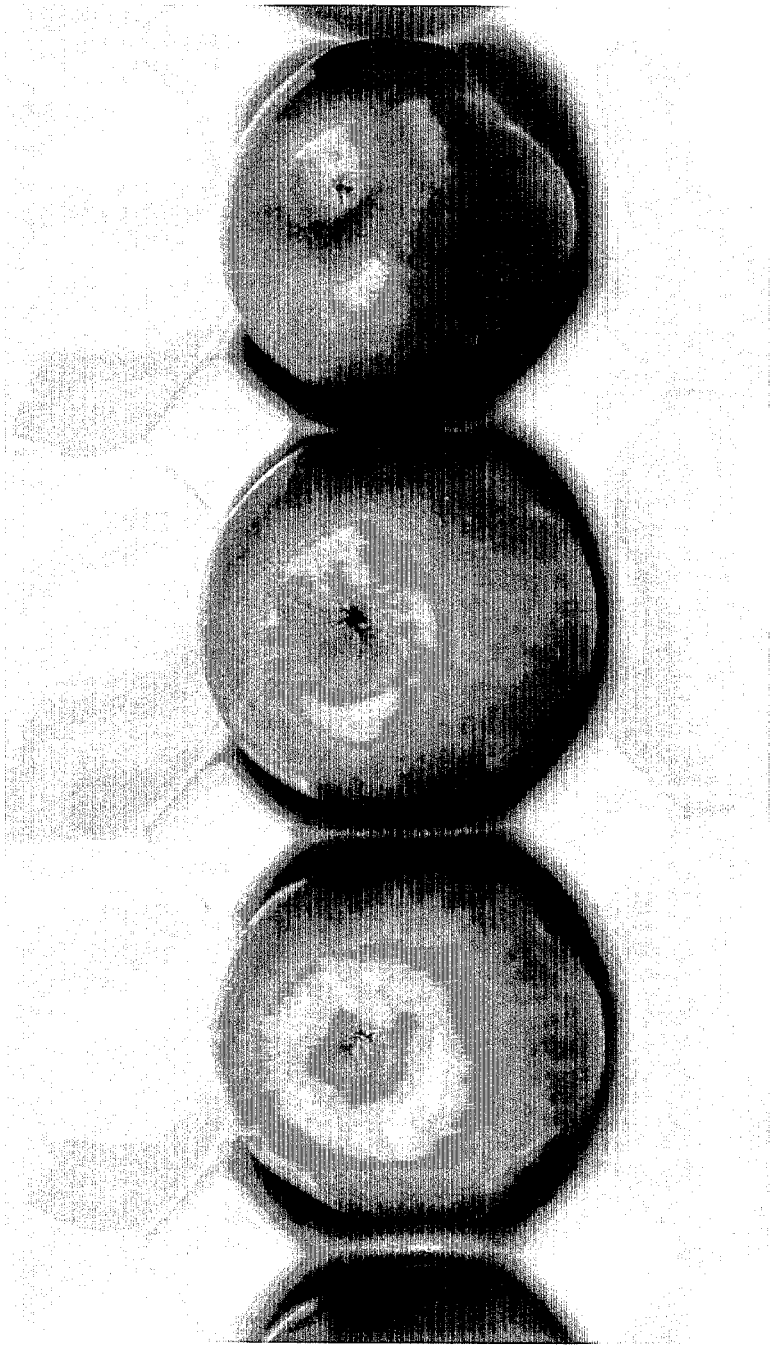
FIG. 3 illustrates the fruit (side view) of TF812 harvest.
Figure 4:
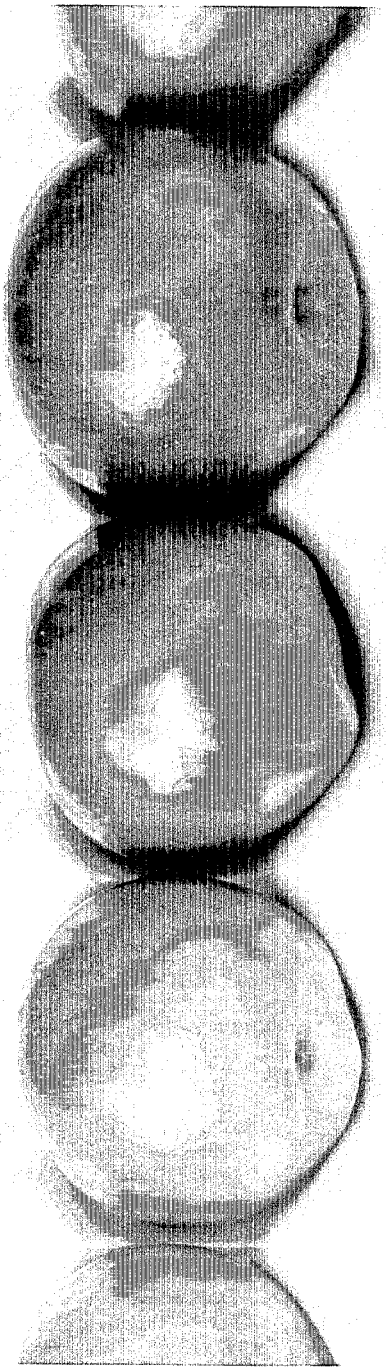
FIG. 4 illustrates the fruit (bottom view) of TF812 at harvest.
Figure 5:
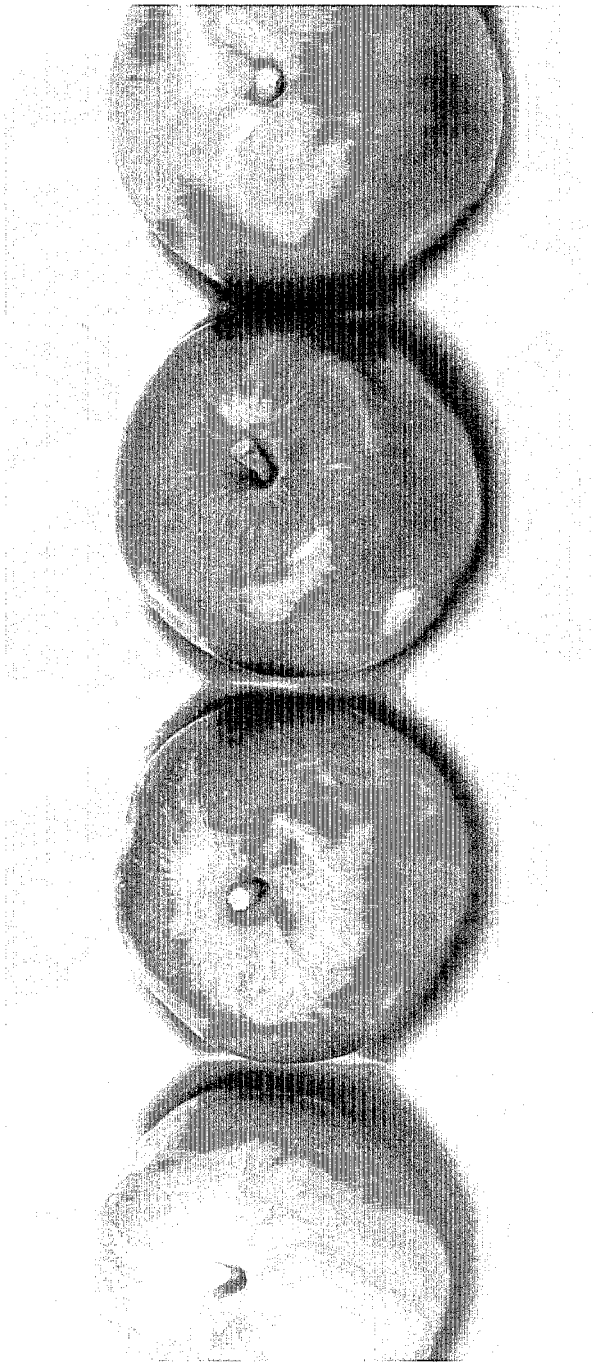
FIG. 5 illustrates the fruit (top view) of TF812 at harvest.

Color descriptions are according to The Horticultural Colour Chart issued by the British Colour Council in collaboration with The British Royal Horticultural Society.

All comparisons are based on the same cultural conditions and same location for the parent variety and TF812. Where a comparison indicates a phenotypic difference exists between the parent variety and TF812, it is of such a nature that it is due to a genetic-based difference between the parent variety and TF812. Thus, these differences are outside the range of variability in degree, pattern, and timing expected solely of the parent variety and are not due to any environmental forces.

Flower:
- *Pedicel.*—1.5 to 2.5 cm in length.
- *Corolla.*—2.0 to 3.0 cm in length.
- *Color.*—Pink.

Comparison with parent variety:
- *Flowering date.*—same as parent variety.
- *Flower size.*—same as parent variety.
- *Flower color.*—same as parent variety.

Pollination: cross-pollination suitable pollinator, "Law Rome".

Fruit:
- *Shape.*—Round to slightly oblate.
- *Size.*—Medium, Axial diameter 5.5 to 6.5 cm, transverse diameter 5.8 to 6.5 cm.
- *Color.*—Garnet Lake (Plate 828), with a dark red blush covering 80–95% of the fruit surface. Date of first coloration: Typically last week of August. Color initiation: Striping forms initially, loses striping close to maturity. Rate of coloring: Colors more rapidly as well as earlier.

*Skin.*—Smooth, waxy with scattered small white dots.

*Stem.*—Short (0.8 to 1.5 cm) slightly clubbed often not extending above the shoulders of the cavity.

*Cavity.*—Smooth to some russeting extending to the shoulders of the cavity wall, obtuse.

*Basin.*—Depth moderate, broad, rounded, non-russeted.

*Calyx.*—Persistent, open, separate at the base, erect to slightly recurved.

*Calyx tube.*—Conical to slightly funnel shaped.

*Stamens.*—Basal.

*Core lines.*—Meeting.

*Core.*—Distal, closed, large.

*Carpels.*—Obovate, smooth.

*Seeds.*—0.6 to 1.0 cm, accuminate, smooth, dark brown.

*Flesh.*—Fine, white, very firm and crisp, slightly sub-acid, very good.

*Susceptibility to Jonathan Spot.*—Not systematically observed, but believed same as parent.

*Lenticels.*—Not systematically observed, but may be larger on average than parent.

*Maturity season.*—Substantially similar to parent variety.

*Keeping quality.*—Excellent.

*Uses.*—Fresh eating, culinary, fresh market.

FRUIT OBSERVATIONS FOR THE YEAR 1992

| | Aug 10 | Aug 14 | Aug 22 | Aug 29 |
|---|---|---|---|---|
| Internal Ethylene Content: | None | .06 ppm | .16 ppm | .2 ppm |
| Flesh Firmness: | 20.3 | 20.1 | 20.2 | 18.6 |
| Starch Index: | 1.2 | 1.3 | 3.5 | 5.7 |
| Color: | 64% | 67% | 83% | 87% |

Comparison with parent variety:

*Harvest date.*—7-10 days earlier than parent variety.

*Post-harvest fruit coloration.*—Typically full coloration at harvest.

*Mature fruit size.*—Approximately 0.25 inch larger than parent variety.

*Mature fruit shape.*—Same as parent variety.

*Mature fruit sugar content.*—Sweeter than parent variety.

*Mature fruit color of exposed fruit.*—Darker than parent variety.

*Production of average tree.*—Believed to be slightly greater than parent, but accurate quantitative data unavailable.

Tree:

*Growth habit.*—Moderately vigorous, spreading, non-spur fruiting habit and in most characteristics similar to parent variety.

*Leaves.*—Medium in size, dark green, simple, obtuse at the base, pointed at the tips, simply serrated at the margins, smooth of the upper surface, dull green and slightly pubescent on the lower surface. Midrib and primary veins raised.

*Leaf size.*—Length: 6.5 to 7.8 cm. Width: 4.0 to 5.8 cm. Length/width Ratio: 1.4 to 1.6 cm.

*Petiole.*—2.5 to 3.6 cm in length, medium thickness, slightly pubescent with some development of red color at the base of the petiole but not extending upward into the leaf blade.

*Thinning.*—Second generation essentially self-thinning to date.

1 *yr. shoots.*—Mostly green to greenish-brown in color, mostly glaborous, thin to medium in caliper, internode length 3.0 to 4.5 cm.

Bark: Same as parent variety.

General: The most striking and economically significant difference between the parent variety and TF812 is the appearance of a much more intense red color of the fruit exterior over a larger area than that of the parent variety. This difference has been consistently observed in comparison of fruit of each of these varieties under the same conditions at the same level of maturity and is due to genetic differences between the varieties rather than to any environmental force. This difference was wholely unexpected and does not fall within any range of variability expressed by the parent variety, leading to the conclusion that TF812 is a whole-tree mutation of the parent variety.

What is claimed is:

1. The new and distinct apple tree as shown and described.

* * * * *